(12) United States Patent
Meyer et al.

(10) Patent No.: US 8,842,271 B2
(45) Date of Patent: Sep. 23, 2014

(54) DEVICE FOR TESTING THE QUALITY OF MICROSTRUCTURIZATION

(75) Inventors: Udo Meyer, Bremen (DE); Susanne Markus, Bremen (DE); Stefan Dieckhoff, Lilienthal (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 27 days.

(21) Appl. No.: 13/809,207

(22) PCT Filed: Jul. 8, 2011

(86) PCT No.: PCT/EP2011/061699
§ 371 (c)(1),
(2), (4) Date: Jan. 9, 2013

(87) PCT Pub. No.: WO2012/007404
PCT Pub. Date: Jan. 19, 2012

(65) Prior Publication Data
US 2013/0107278 A1    May 2, 2013

(30) Foreign Application Priority Data
Jul. 12, 2010    (DE) .......................... 10 2010 031 227

(51) Int. Cl.
| | | |
|---|---|---|
| *G01N 21/00* | (2006.01) | |
| *G01N 21/956* | (2006.01) | |
| *G01B 11/24* | (2006.01) | |
| *G01N 21/47* | (2006.01) | |
| *G01B 11/30* | (2006.01) | |

(52) U.S. Cl.
CPC .............. *G01B 11/24* (2013.01); *G01N 21/956* (2013.01); *G01N 21/4788* (2013.01); *G01B 11/303* (2013.01)
USPC ...................................... 356/237.2; 356/445

(58) Field of Classification Search
CPC .................. G01N 2021/8822; G01N 21/9501; G01N 21/956; G01B 11/30; G01B 11/303; G01B 11/306
USPC .................... 356/237.1–237.5, 445–448, 600
See application file for complete search history.

(56) References Cited

U.S. PATENT DOCUMENTS

| | | |
|---|---|---|
| 4,598,997 A | 7/1986 | Steigmeier et al. |
| 5,276,498 A | 1/1994 | Galbraith et al. |

(Continued)

FOREIGN PATENT DOCUMENTS

| | | |
|---|---|---|
| DE | 100 27 439 | 5/2000 |
| EP | 1 065 499 | 1/2001 |
| EP | 1 589 496 | 10/2005 |

*Primary Examiner* — Hoa Pham
(74) *Attorney, Agent, or Firm* — Preti Flaherty Beliveau & Pachios LLP (57) ABSTRACT

A device for testing the quality of microstructurization of a surface (2) having a known target microstructurization quality, comprising a radiation source (1) for coherent radiation, a first detector (10) and a second detector (4) and a masking system, all of which are set up and arranged with respect to one another so that radiation emitted by the radiation source (1) onto the surface (2) produces a diffraction pattern, wherein the diffraction maximum of order n of the diffraction pattern without the masking system would impinge on the first detector (10), the masking system prevents 80% of the photons that are assigned to the diffraction maximum of order n from impinging on the first detector and the diffraction maximum of order a of the diffraction pattern impinges on the second detector (4), wherein n is selected from the group consisting of 1, 2, 3, 4, 5, 6, 7, 8, 9 and 10 and a is selected from the group consisting of 1, 2, 3, 4, 5, 6, 7, 8, 9 and 10 and a≠n.

12 Claims, 2 Drawing Sheets

(56) References Cited

U.S. PATENT DOCUMENTS

| | | | |
|---|---|---|---|
| 6,914,683 B1 * | 7/2005 | Baumgart et al. | 356/512 |
| 7,460,981 B2 * | 12/2008 | Bultman et al. | 702/155 |
| 2003/0132405 A1 | 7/2003 | Some | |
| 2008/0291436 A1 * | 11/2008 | Aiko et al. | 356/237.2 |

* cited by examiner

DEVICE FOR TESTING THE QUALITY OF MICROSTRUCTURIZATION

BACKGROUND OF THE INVENTION

Field of the Invention

The invention relates to a device for testing the microstructurization quality of a surface when the target microstructurization quality is known. It further relates to an arrangement comprising said device and a microstructuring device. The invention further relates to a method for testing the microstructurization quality of a surface with known target microstructurization quality and a method for the microstructuring of a surface. It further relates to the use of a device according to the invention for testing the microstructurization quality of a surface and the use of an arrangement according to the invention for the microstructuring of a surface, wherein quality testing and optionally control of the operating mode of the microstructuring device when a minimum quality standard is not met can take place simultaneously.

Through a suitable three-dimensional configuration of surfaces in the submillimeter range it is possible to provide the surfaces with particular properties. A familiar example is the lotus effect, by which liquids are shed more easily from surfaces. This three-dimensional structuring in the submillimeter range (microstructurization) is in the ideal case a regularly repeating pattern. These are also known as riblet structures. Such structures are especially interesting in the area of vehicle technology and turbine technology. Here they serve primarily for reducing frictional drag. Preferred applications for said microstructuring/riblet structures are surfaces or sections of surfaces of aircraft, especially their supporting surfaces and fuselage, of rail vehicles, especially locomotive and wagon bodywork, automobiles, ships, especially their hulls and screw propellers, wind energy installations, especially their rotor blades, turbines, especially their rotor and stator blades and internal surfaces of tubes, especially for pipelines.

For the microstructuring to be able to perform its function, it must achieve a minimum quality. The requirements are different in different applications, and naturally they are particularly high in the area of aeronautics. Accordingly, quality assurance of the applied riblet structures is desirable in particular in the aeronautics field, as the three-dimensional configurations of the surface in the submillimeter range must in some applications be exact to a few micrometers.

In principle, for quality assurance of microstructurization, a number of topology-imaging techniques are available, for example focus variation microscopy, fringe projection, low-coherence interferometry and techniques based on the diffraction of light waves. All the existing known methods require relatively expensive equipment and/or are time-consuming, if the accuracy required in the aviation industry must be fulfilled. Presumably for these reasons, at present no corresponding technique is applied regularly for monitoring the structures used in the aviation industry.

DESCRIPTION OF RELATED ART

Diffraction-based methods for imaging periodic structures are already known from other technical areas. We may mention for example US2008291436A, JP2008058248A, JP2007170827A, DE102004008474A, WO04068070A and U.S. Pat. No. 6,914,683B.

In U.S. Pat. No. 3,748,047A, reflected and diffracted light is compared, to obtain information about surface quality. Masking is also used, but the method disclosed in this document is not suitable in doubtful cases for differentiating between very good microstructurization and absence of microstructurization.

BRIEF SUMMARY OF THE INVENTION

Against this background, the problem to be solved by the present invention was to provide a device for testing the quality of microstructurization of a surface, which is of relatively simple construction, with relatively inexpensive components, which is simple to operate and/or is also able to indicate complete absence of microstructurization in parallel with determination of quality.

This problem is solved with a device for testing the quality of microstructurization of a surface (2) with known target microstructurization quality, comprising a radiation source (1) for coherent radiation, a first detector (10), a second detector (4) and a masking system, which are set up and arranged with respect to one another so that
  (a) radiation emitted from the radiation source (1) onto a surface (2), which is provided with microstructurization of the target quality, produces a diffraction pattern,
  (b) the diffraction maximum of order n of the diffraction pattern would, without the masking system, impinge on the first detector (10),
  (c) the masking system prevents 80% of the photons that are to be assigned to the diffraction maximum of order n, from impinging on the first detector and
  (d) the diffraction maximum of order a of the diffraction pattern impinges on the second detector (4),
wherein n is selected from the group consisting of 1, 2, 3, 4, 5, 6, 7, 8, 9 and 10 and a is selected from the group consisting of 1, 2, 3, 4, 5, 6, 7, 8, 9 and 10 and a≠n.

Microstructuring (riblet structuring) in the sense of this application is a spatial/periodic structure (surface topography). As mentioned above, this surface topography comprises structural elements in the submillimeter range, preferably with depressions in the range from 0.05 to 500 µm, more preferably 0.5 to 200 µm, more preferably from 5 to 100 µm and especially preferably 20 to 50 µm. The distances between adjacent peaks in the surface topography are preferably 0.05 to 500 µm, more preferably from 5 to 250 µm and especially preferably 10 to 200 µm. If the peaks are plateaux, the distance values are in each case to be reckoned from the outer edge of one plateau to the outer edge of the next plateau.

Preferred structuring elements for microstructuring are prisms, plateaux and parabola-shaped ridges.

Producing microstructurization in the sense of this application means that a surface is provided with microstructurization. This can take place for example by embossing of metal or paint. As a rule this is performed with a die, which represents a negative image of the desired surface topography. Another possibility is ablative structuring of the surface using a laser. The structure can also be produced by direct milling into the surface.

The "target microstructurization quality" in the sense of this application is the quality that is achieved when the surface topography defined by the die is transferred without error onto a corresponding surface. The target microstructurization quality is in case of doubt determined directly on the die and converted to the negative.

"Microstructurization quality" in the sense of the application means the extent of deviation from the target microstructurization quality. In other words: the smaller the deviation from the target microstructurization quality, the higher the microstructurization quality.

If microstructures are irradiated with coherent radiation, such as a laser beam for example, along with the reflected light there is also formation of a diffraction pattern.

A masking system in the sense of the present application is preferably a device that prevents radiation (at least partially) entering the space which, viewed from the direction of propagation of the radiation, is located behind the device (masking system).

"Photons that are to be assigned to a diffraction maximum" are those photons that are to be assigned to the integral under the intensity curve, wherein the integral is delimited laterally by the minima adjacent to the maximum.

Preferred radiation sources in the sense of the present invention are lasers, especially diode lasers.

The nature of the diffraction patterns (and of the diffraction diagrams representing this pattern) is influenced by the microstructurization quality. Microstructuring of high quality provides a simple diffraction image, for which the maxima all lie in a straight line, or on a circle and most of the intensity of the diffracted radiation ends up in the maxima. A deviation from the target microstructurization quality, for example a rounding of crests, scratches, defects etc. leads to a change in the diffraction diagrams. As a result, in the original regions of maximum intensity there is a decrease in intensity. Accordingly, a higher intensity will be measurable in regions outside of the maxima.

This means that a simple quality criterion is the intensity of the diffracted radiation outside of the original intensity maxima. The radiation can be diffracted by the periodic structure of the microstructurization onto a detector. Detector, in the sense of the invention, is a device that is sensitive to the radiation used, and is able, as a function of the radiation intensity, to produce a signal that is analogous to the radiation intensity.

A first detector and a second detector are provided in the device according to the invention. The function of the first detector is to determine the deviation from the target structuring quality, when microstructurization is present. In order to achieve an improved signal strength, it is envisaged in devices according to the invention that a masking system prevents ≥80% of the photons, preferably ≥85%, more preferably ≥90% and especially preferably ≥95% of the photons, which are to be assigned to the diffraction maximum of the respective order n, from impinging on the first detector.

Naturally it is preferable that in the sense of the application n=1 and a=2, 3 or 4.

Because for the case of a high microstructurization quality, a high proportion of photons are prevented from impinging on the first detector, when there is deviation from the target microstructurization quality a particularly high (relative) signal reaches the first detector.

In this connection it should once again be emphasized that the microstructurization quality determined with the device according to the invention is always to be considered in relation to the target microstructurization quality.

Because during use for the device according to the invention the target microstructurization quality is known (for example the die already exists), it is easy for a person skilled in the art to select a suitable radiation source, appropriate to the given circumstances. Moreover, he will have no difficulty in arranging the elements of the device described above in relation to one another so that a meaningful measurement is possible. We may mention in particular the distances from the radiation source to the surface to be tested, the inclination of the radiation impinging on the surface to be tested, the distance of the detectors from the surface to be tested and the angle of the detectors to the corresponding surface.

The function of the second detector in the device according to the invention is to ensure that a (minimum) microstructurization is present at all. Thus, a case could arise in which, in the absence of microstructurization (or with a very poor microstructurization quality), there is total reflection of the radiation impinging on the surface. Total scattering could also occur. The consequence of this would be that, on the first detector, a signal would be produced that would falsely indicate high microstructurization quality: outside of the region (covered by the masking system) of the diffraction maximum of order n, relatively little radiation would impinge on the detector and would thus apparently indicate the absence of spurious diffraction caused by low microstructurization quality. Accordingly it is advantageous that the second detector identifies whether diffraction patterns are present at all. Of course, it is also possible to equip the second detector with a masking system, which for example prevents photons impinging on the detector, if they are photons that are not to be assigned to the diffraction maximum of diffraction order a.

As mentioned above, it is preferred that a>n.

It is preferred according to the invention that the radiation source irradiates an area of ≤10 cm$^2$, preferably ≤5 cm$^2$, more preferably ≤1 cm$^2$, and especially preferably ≤5 mm$^2$ on the surface to be tested.

With a relatively small irradiated area it is also possible to determine the quality of the microstructurization in the region of curvatures with a sufficient accuracy. Thus, a person skilled in the art knows that in the microstructurization of areas with small radius of curvature, the radiation area must be reduced in size correspondingly.

As also already mentioned above, the position of the detectors (and optionally the size of the irradiated area on the surface to be tested) must be adapted to the respective (target) microstructurization, and of course this also applies to the size and the position of the respective masking system.

A particular advantage of the device according to the invention is that it can determine the microstructurization quality in real time. The construction of the device according to the invention is simple and consists of a small number of inexpensive components. No moving parts are absolutely necessary, and no complicated optics. Accordingly, it is preferred according to the invention that the device according to the invention is free from prisms.

Despite the relatively simple design, the use of the device according to the invention leads to a very sensitive method for measuring the microstructurization quality of a surface, i.e. in this case especially for deviations from the target microstructurization quality.

Based on the foregoing, it is preferred according to the invention that the first detector and the second detector are arranged at an angle to one another.

"Arranged at an angle" means in this case that they are not parallel to one another.

With a suitable choice of angle to one another, it is therefore ensured that the radiation of the diffraction maximum that is decisive in each case for the detector (of order a or of order n) impinges normally on the respective detector. Moreover, it is preferred according to the invention that the detectors according to the invention are selected with respect to their size in such a way that as far as possible they are still in the region of the diffraction maxima of the adjacent orders (n±1 or a±1), of course preferably avoiding impingement of the radiation of the "diffraction maximum" of zero order on one of the detectors.

A preferred device according to the invention comprises a signal evaluator, for comparing the signal produced by the first detector with a target value Z1 and/or the signal produced by the second detector with a target value Z2.

The advantage of this form of determination is that it is possible, via an output device (which preferably also forms part of the device according to the invention), to communicate information about the microstructurization quality or the deviation of the microstructurization quality from the target microstructurization quality.

This signal evaluator can for example be a computer, which compares the signals produced by the detectors with an assigned target value. The target value Z1 and Z2 is in each case the value that corresponds to the target microstructurization quality. As mentioned above, said value can be determined in relation to the microstructurization die that is used.

A device according to the invention is further preferred, wherein the signal evaluator is set up for comparing the signal produced by the first detector with a limit G1 and/or the signal produced by the second detector with a limit G2.

The limits G1 and G2 represent a threshold value that depends on the target microstructurization quality, up to which a deviation from the target microstructurization quality can still be tolerated. These limits can be selected by a person skilled in the art in relation to the intended application of the microstructurization.

Defining such a limit has the advantage that for the case when it is not reached in the direction of inadequate microstructurization quality (or is exceeded, depending on the definition of the limit) a corresponding warning signal can be produced and/or an adjustment in the microstructurization (see below).

An arrangement comprising a device according to the invention and a microstructuring device also form part of the invention.

A microstructuring device in the sense of this application is a device that is suitable for applying a microstructurization on a surface. It can for example be embossing rolls (for the microstructurization of hard surfaces) or die systems (for the microstructurization of thermosetting surfaces).

The advantage of such an arrangement according to the invention is that immediately after applying or producing a corresponding microstructurization, its quality can be tested.

Preferred, according to the invention, is an arrangement according to the invention that comprises a device according to the invention, wherein the device according to the invention comprises a signal evaluator for comparing the signal produced by the first detector with a target value Z1 and a limit G1 and/or for comparing the signal produced by the second detector with a target value Z2 and a limit G2. Said preferred arrangement according to the invention further comprises a control line for communicating a control signal for altering the operating mode of the microstructuring device.

Altering of the operating mode of course takes place in the sense of the invention in order to produce an improved microstructurization quality, for example for the case when one of the limits G1 or G2 is not achieved, in the direction of inadequate microstructurization quality. A corresponding change of the operating mode of the microstructuring device can for example be an increased pressure (or a decreased pressure), an altered operating speed, a different irradiation intensity from the curing lamps or a different wavelength of the irradiation lamp.

In this connection, it is of course apparent to a person skilled in the art that the microstructuring device does not necessarily only comprise the respective die, but can comprise further elements, for example applicators for thermosetting materials, curing devices such as UV lamps for example, and flexible coating rolls.

The invention further relates to a method for testing the microstructurization quality of a surface in the case of a known target microstructurization quality, comprising the steps:
A) providing a device according to the invention or an arrangement according to the invention,
B) providing a surface to be tested,
C) aligning the device or the arrangement with the surface to be tested, so that in the case when the surface is provided with a microstructurization of the target quality
   (a) radiation emitted by the radiation source onto the surface produces a diffraction pattern,
   (b) the diffraction maximum of order n of the diffraction pattern would, without the masking system, impinge on the first detector,
   (c) the masking system prevents 80% of the photons that are to be assigned to the diffraction maximum of order n from impinging on the detector and (d) the diffraction maximum of order a of the diffraction pattern impinges on the second detector, and
D) processing of the signal produced by the first detector and of the signal produced by the second detector.

In this method, the device according to the invention is used appropriately. As mentioned above, step C) can be undertaken without difficulty by a person skilled in the art—especially with known target microstructurization quality—including in particular the aligning of the device with the surface to be tested. Step D serves for example for output of information via a display. During the processing, preferably the signals of the detectors are compared with the target values Z1, Z2 and/or the limits G1, G2.

The invention also relates to a method of microstructuring a surface, comprising the steps:
A) providing a preferred arrangement according to the invention as described above (with signal evaluator for comparing the target values Z1, Z2, E1 and/or G2 and control line, see above)
B) providing a surface to be microstructured,
C) microstructuring the surface with the arrangement, wherein in parallel a method according to the invention for testing the microstructurization quality of the surface (that has just been) microstructured is carried out and if one of the limits G1 or G2 is undershot, a control signal is transmitted via a control line (9) for altering the operating mode of the microstructuring device (16), so that the quality of the microstructurization produced corresponds more or completely to the target microstructurization quality.

With this method according to the invention it is possible to monitor the microstructurization quality in situ during application and optionally intervene in the microstructurization process, so that if the result is below a minimum quality of the microstructurization, the microstructurization applied subsequently complies with the minimum quality or is even close to the target quality. Of course, in the sense of the invention it is also possible, with even a slight deviation from the target quality, to make a corresponding adjustment, so that there is a constant regulating process.

A use of a device according to the invention or of an arrangement according to the invention for testing the quality of microstructurization of a surface in the case of known target microstructurization quality and a use of an arrangement according to the invention for the microstructuring of a surface also form part of the invention.

These applications lead in each case to the advantages described above.

BRIEF DESCRIPTION OF THE DRAWINGS

The invention is explained in more detail below with a practical example and on the basis of drawings, which show:

In FIGS. 2 and 3, the filled black points (schematic) correspond in each case to the masking system.

In the figures, the reference symbols have the following meanings:
- 1 radiation source, preferably a laser,
- 2 surface to be tested,
- 3 diffracted radiation, of first order,
- 4 second detector,
- 5 diffracted radiation, of higher order,
- 6 housing,
- 7 signal line,
- 8 signal evaluator,
- 9 signal line,
- 10 first detector,
- 11 idealized diffraction image of a riblet structure on the masked detector,
- 12 idealized diffraction image of an idealized riblet structure on the masked detector,
- 13 masked detector,
- 14 idealized diffraction image of an ideal riblet structure on the unmasked detector and
- 16 microstructuring device

DETAILED DESCRIPTION OF THE INVENTION

Figure 1:
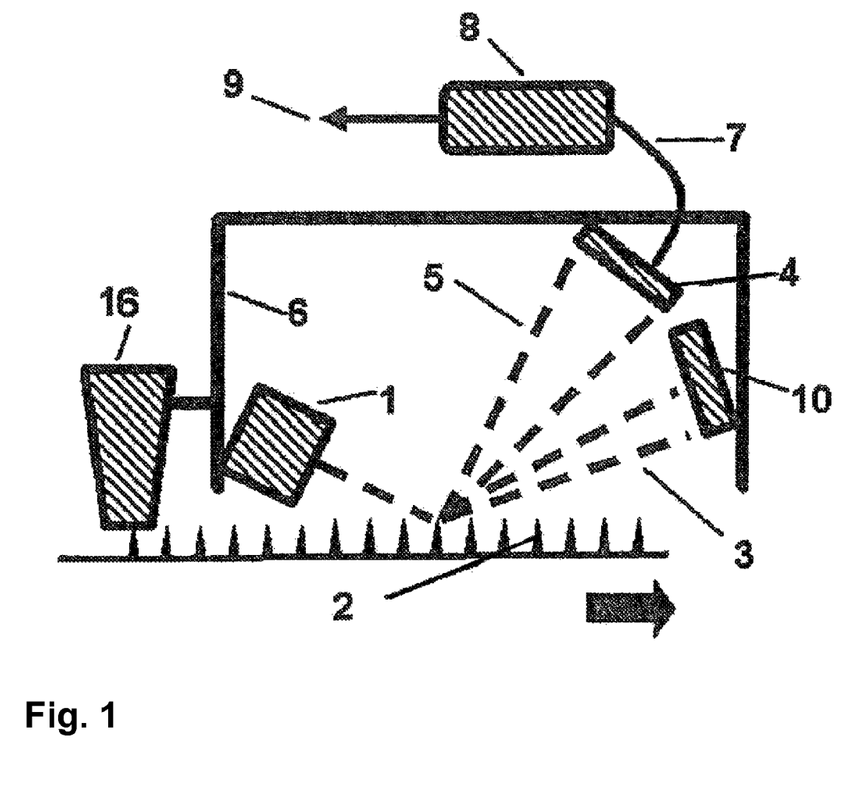
FIG. 1 a schematic representation of an arrangement according to the invention.
Figure 2:
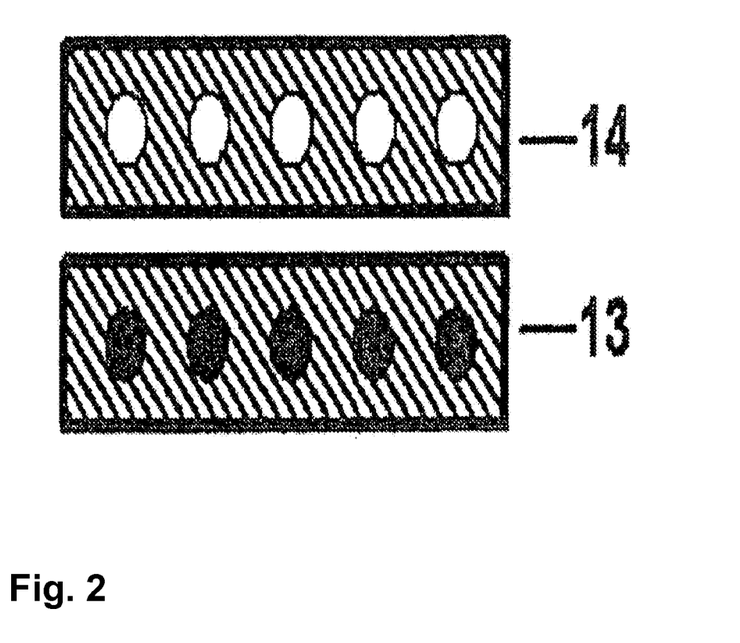
FIG. 2 a masked detector (bottom) and an idealized diffraction image of an ideal riblet structure on the unmasked detector (top) and FIG. 3 an idealized diffraction image of a disturbed riblet structure on the masked detector (bottom) and an idealized diffraction image of an ideal riblet structure on the masked detector.
Figure 3:
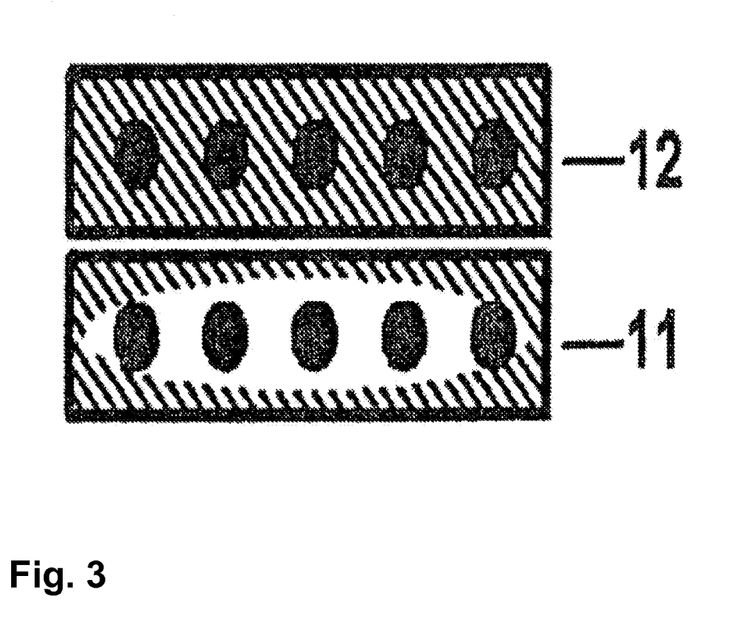

FIG. 1 shows a simple and desirable configuration of the arrangement according to the invention. As indicated by the arrow in FIG. 1, it is possible that the arrangement according to the invention is stationary, while the surface to be structured is moved past the arrangement. Of course, the reverse is also possible, with the arrangement being moved past the surface to be microstructured. Referring to FIG. 1, the radiation source 1, in this case a laser, emits laser light of a wavelength suitable for the target microstructurization quality onto the surface to be tested. This light is diffracted (inter alia) on the surface. Moreover, the distances and arrangements of the laser 1, of the surface to be tested 2, of the first detector 10 and of the second detector 4 with respect to one another are selected in such a way that the first detector 10 is located in the region of the diffracted beam of first order (3) and the second detector 4 is located in the region of the diffracted beam of higher order (here for example of second order). The device is housed in a housing 6 and the two detectors 4, 10 are connected via a control line 7 to a signal evaluator 8 (control line 7 for the first detector 10 not shown). In FIG. 1, the first detector 10 is masked with a mask as shown with reference symbol 13 in FIG. 2 (not shown in FIG. 1).

As a result, a substantial proportion of the photons that are assigned to the diffraction maximum of first order are precluded from impinging on the first detector 10. Therefore the detector sensitively determines deviations from the target microstructurization quality, i.e. photons that would lie outside of the diffraction pattern of the target microstructurization quality. The first detector 10 transmits a corresponding signal to the signal evaluator 8. The second detector 4 determines whether a diffracted beam of higher order (here of second order) is present. It thus determines whether a diffraction pattern is present at all and thus registers a severe microstructuring defect or a complete absence of microstructurization, for the case when no diffraction pattern is present.

The second detector 4 also transmits a corresponding signal via the control line 7 to the signal evaluator 8. The signal evaluator 8 compares the values measured by the detectors with the target values Z1 and Z2, which have previously been programmed into the signal evaluator depending on the target microstructurization quality. In addition the signal evaluator 8 compares whether a limit G1 or G2 has not been met, in the direction of inadequate microstructurization quality. This would be the case for example if the first detector measures an excessively high light intensity or the second detector measures one that is too low. These limits are also dependent on the target microstructurization quality and the tolerable deviation from this.

If one of these limits G1 or G2 is not met, in the sense of inadequate microstructurization quality, the signal evaluator 8 transmits a signal via the signal line 9 to the microstructuring device 16, whereby the operating mode of the microstructuring device 16 is altered so that the microstructurization quality of the microstructuring that is produced by the microstructuring unit 16 is improved.

Accordingly, in an arrangement according to the invention as in FIG. 1, with very coarsely disturbed microstructurization, no notable proportion of the light is diffracted on the surface. In this case the second detector 4 registers an absence of diffraction patterns of higher order. If, however, a sufficient intensity is registered on the second detector 4, a microstructurization is present. If the first detector 10 simultaneously indicates a very low intensity, then the quality of the microstructurization is close to the target microstructurization quality. However, if the intensity on the first detector 10 is too high, the quality of the microstructurization is unsatisfactory.

As already described above several times, the distances of the individual components from one another, and the configuration of the masking system, are adapted to the respective target microstructurization or the quality thereof.

The invention claimed is:

1. Device for testing the quality of microstructurization of a surface in the case of known target microstructurization quality, comprising a radiation source for coherent radiation, a first detector, a second detector and a masking system, which are set up and arranged with respect to one another so that
    (a) radiation emitted by the radiation source onto a surface, which is provided with a microstructurization of the target quality, produces a diffraction pattern,
    (b) the diffraction maximum of order "n" of the diffraction pattern would, without the masking system, impinge on the first detector,
    (c) the masking system prevents ≥80% of the photons that are to be assigned to the diffraction maximum of order "n" from impinging on the detector and
    (d) the diffraction maximum of order "a" of the diffraction pattern impinges on the second detector,
wherein "n" is selected from the group consisting of 1, 2, 3, 4, 5, 6, 7, 8, 9 and 10 and "a" is selected from the group consisting of 1, 2, 3, 4, 5, 6, 7, 8, 9 and 10 and a≠n.

2. Device according to claim 1, wherein the first detector and the second detector are arranged at an angle to one another.

3. Device according to claim 1, comprising a signal evaluator, for comparing one of the signal produced by the first detector with a target value Z1 and the signal produced by the second detector with a target value Z2.

4. Device according to claim 3, wherein the signal evaluator is set up for comparing one of the signal produced by the first detector with a limit G1 and the signal produced by the second detector with a limit G2.

5. Arrangement, comprising a device according to claim 1 and a microstructuring device.

6. Arrangement according to claim 5, comprising a device testing the quality of microstructurization of a surface in the case of known target microstructurization quality, comprising a radiation source for coherent radiation, a first detector, a second detector and a masking system, which are set up and arranged with respect to one another so that
   (a) radiation emitted by the radiation source onto a surface, which is provided with a microstructurization of the target quality, produces a diffraction pattern,
   (b) the diffraction maximum of order "n" of the diffraction pattern would, without the masking system, impinge on the first detector,
   (c) the masking system prevents ≥80% of the photons that are to be assigned to the diffraction maximum of order "n" from impinging on the detector and
   (d) the diffraction maximum of order "a" of the diffraction pattern impinges on the second detector,
wherein "n" is selected from the group consisting of 1, 2, 3, 4, 5, 6, 7, 8, 9 and 10 and "a" is selected from the group consisting of 1, 2, 3, 4, 5, 6, 7, 8, 9 and 10 and a≠n,
   wherein:
   the signal evaluator is set up for comparing one of the signal produced by the first detector with a limit G1 and the signal produced by the second detector with a limit G2; and
   further comprising a control line for communicating a control signal for altering the operating mode of the microstructuring device.

7. Method for the microstructuring of a surface using an arrangement according to claim 5.

8. Method for testing the microstructurization quality of a surface in the case of a known target microstructurization quality, comprising the steps:
   A) providing a device according to an arrangement according to claim 5,
   B) providing a surface to be tested,
   C) aligning the device or the arrangement with the surface to be tested, so that in the case when the surface is provided with a microstructurization of the target quality
      (a) radiation emitted by the radiation source onto the surface produces a diffraction pattern,
      (b) the diffraction maximum of order "n" of the diffraction pattern would, without the masking system, impinge on the first detector,
      (c) the masking system prevents ≥80% of the photons that are to be assigned to the diffraction maximum of order "n", from impinging on the detector and
      (d) the diffraction maximum of order "a" of the diffraction pattern impinges on the second detector, and
   D) processing of the signal produced by the first detector and of the signal produced by the second detector,
wherein "n" is selected from the group consisting of 1, 2, 3, 4, 5, 6, 7, 8, 9 and 10 and "a" is selected from the group consisting of 1, 2, 3, 4, 5, 6, 7, 8, 9 and 10 and a≠n.

9. Method for testing the quality of microstructurization of a surface in the case of known target microstructurization quality using a device according to an arrangement according to claim 5.

10. Method for testing the microstructurization quality of a surface in the case of a known target microstructurization quality, comprising the steps:
    A) providing a device according to claim 1,
    B) providing a surface to be tested,
    C) aligning the device or the arrangement with the surface to be tested, so that in the case when the surface is provided with a microstructurization of the target quality
       (a) radiation emitted by the radiation source onto the surface produces a diffraction pattern,
       (b) the diffraction maximum of order "n" of the diffraction pattern would, without the masking system, impinge on the first detector,
       (c) the masking system prevents ≥80% of the photons that are to be assigned to the diffraction maximum of order "n", from impinging on the detector and
       (d) the diffraction maximum of order "a" of the diffraction pattern impinges on the second detector, and
    D) processing of the signal produced by the first detector and of the signal produced by the second detector,
wherein "n" is selected from the group consisting of 1, 2, 3, 4, 5, 6, 7, 8, 9 and 10 and "a" is selected from the group consisting of 1, 2, 3, 4, 5, 6, 7, 8, 9 and 10 and a≠n.

11. Method for testing the quality of microstructurization of a surface in the case of known target microstructurization quality, using a device according to claim 1.

12. Method of microstructuring a surface, comprising the steps:
    A) providing an arrangement comprising a device testing the quality of microstructurization of a surface in the case of known target microstructurization quality, comprising a radiation source for coherent radiation, a first detector, a second detector and a masking system, which are set up and arranged with respect to one another so that
       (a) radiation emitted by the radiation source onto a surface, which is provided with a microstructurization of the target quality, produces a diffraction pattern,
       (b) the diffraction maximum of order "n" of the diffraction pattern would, without the masking system, impinge on the first detector,
       (c) the masking system prevents ≥80% of the photons that are to be assigned to the diffraction maximum of order "n" from impinging on the detector and
       (d) the diffraction maximum of order "a" of the diffraction pattern impinges on the second detector,
          wherein "n" is selected from the group consisting of 1, 2, 3, 4, 5, 6, 7, 8, 9 and 10 and "a" is selected from the group consisting of 1, 2, 3, 4, 5, 6, 7, 8, 9 and 10 and a≠n:
          wherein the signal evaluator is set up for comparing one of the signal produced by the first detector with a limit G1 and the signal produced by the second detector with a limit G2; and further comprising a microstructuring device;
wherein the signal evaluator is set up for comparing one of the signal produced by the first detector with a limit G1 and the signal produced by the second detector with a limit G2,
and a control line for communicating a control signal for altering the operating mode of the microstructuring device;

B) providing a surface to be microstructured,

C) microstructuring the surface with the arrangement, wherein in parallel, a method according to claim 7 is carried out and if one of the limits G1 or G2 is undershot, a control signal is transmitted via a control line for altering the operating mode of the microstructuring device, so that the quality of the microstructurization produced corresponds more or completely to the target microstructurization quality.

* * * * *

UNITED STATES PATENT AND TRADEMARK OFFICE
CERTIFICATE OF CORRECTION

| | |
|---|---|
| PATENT NO. | : 8,842,271 B2 |
| APPLICATION NO. | : 13/809207 |
| DATED | : September 23, 2014 |
| INVENTOR(S) | : Udo Meyer et al. |

It is certified that error appears in the above-identified patent and that said Letters Patent is hereby corrected as shown below:

Title page, item (57) ABSTRACT, line 10,

"first detector (10), the masking system prevents 80% of the"

Should read:

-- first detector (10), the masking system prevents ≥ 80% of the --

Signed and Sealed this
Thirty-first Day of March, 2015

Michelle K. Lee
*Director of the United States Patent and Trademark Office*